United States Patent [19]
Terrell

[11] 3,987,111
[45] Oct. 19, 1976

[54] PRODUCTS AND PROCESS

[75] Inventor: Ross C. Terrell, Plainfield, N.J.

[73] Assignee: Airco, Inc., Montvale, N.J.

[22] Filed: Nov. 20, 1975

[21] Appl. No.: 633,763

Related U.S. Application Data

[62] Division of Ser. No. 367,596, June 6, 1973, Pat. No. 3,947,595, which is a division of Ser. No. 170,954, Aug. 11, 1971, Pat. No. 3,764,706.

[52] U.S. Cl............................................. 260/614 F
[51] Int. Cl.² ......................................... C07C 43/12
[58] Field of Search................................. 260/614 F

[56] References Cited
UNITED STATES PATENTS 3,746,769  7/1973  Terrell............................. 260/614 F

*Primary Examiner*—Howard T. Mars
*Attorney, Agent, or Firm*—Roger M. Rathbun; Edmund W. Bopp; H. Hume Mathews

[57] ABSTRACT

This disclosure is directed to novel ethers of the formula:

$$CF_3CH_aX_b-O-CF_2CH_cF_dCl_e$$

wherein X is fluorine, chlorine or bromine, preferably fluorine, $a$ is 1 or 2, $b$ is 0 or 1, $a$ plus $b$ are 2, preferably both $a$ and $b$ being 1, $c$ is 0 or 1, $d$ is 0 to 2, $e$ is 0 to 2, $c$ plus $d$ plus $e$ are 3, preferably each of $c$, $d$, and $e$ is 1, and $a$ plus $c$ are 1 or 2, preferably 2, with the proviso that when $e$ is 1 or 2, X is fluorine or bromine, preferably fluorine. The compounds having less than 8 fluorine atoms per molecule are useful as anesthetics, and all of the compounds are useful as solvents and dispersants for fluorinated materials. A highly preferred compound useful as an anesthetic is 1,2,2,2-tetrafluoroethyl 1',1',2'-trifluoro-2'-chloroethyl ether.

1 Claim, No Drawings

PRODUCTS AND PROCESS

This is a Division of Application Ser. No. 367,596, filed June 6, 1973, now U.S. Pat. No. 3,947,595, which in turn was a Division application of Ser. No. 170,954, filed Aug. 11, 1971, now U.S. Pat. No. 3,764,706, issued Oct. 10, 1973.

This invention relates to the novel ethers of the formula:

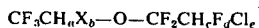

$$CF_3CH_aX_b-O-CF_2CH_cF_dCl_e.$$

wherein X is fluorine, chlorine or bromine, preferably fluorine, $a$ is 1 or 2, $b$ is 0 or 1, $a$ plus $b$ are 2, preferably both $a$ and $b$ being 1, $c$ is 0 or 1, $d$ is 0, 1 or 2, $e$ is 0, 1 or 2, $c$ plus $d$ plus $e$ are 3, preferably each of $c$, $d$, and $e$ is 1, and $a$ plus $c$ are 1 or 2, preferably 2, with the proviso that when $e$ is 1 or 2, X, if present, is fluorine or bromine, preferably fluorine. Preferably when $e$ is 1 or 2, $b$ is 1. These ethers which have less than 8 fluorine atoms per molecule, especially 6 or 7 fluorine atoms per molecule, can be used to produce anesthesia in anesthetic-susceptible mammals. All of the ethers of this invention are easily miscible with other organic liquids, including fats and oils, and have useful solvent properties. These ethers are useful, for example, as solvents for fluorinated olefins and other fluorinated materials such as fluorowaxes. The ethers can also be used to prepare pastes and dispersions of such fluorine-containing materials useful for coatings and the like, and can be used as degreasing agents. In the latter capacity, for example, the ether compounds of this invention can be used as solvents to remove grease or other oily substances from metal surfaces that are to be painted.

A highly preferred compound of the invention is 1,2,2,2-tetrafluoroethyl 1',1',2'-trifluoro-2'-chloroethyl ether having the formula $CF_3CHF-O-CF_2CHFCl$. This compound is normally a clear, colorless liquid with an ethereal odor. This ether has the following physical properties: b.p. 65.5° C. at 760 mm.; vapor pressure 175 mm. at 25° C.; specific gravity 1.52; and molecular weight 234.5. The compound is nonflammable, soda lime stable, and a potent anesthetic for inhalation anesthetic-susceptible mammals.

The compounds of the present invention can be prepared by the fluorination, chlorination or bromination of the corresponding halogen-containing ethers to substitute one or two additional halogen atoms per molecule in place of hydrogen atoms of the feed. The ethers of the invention may also be formed by the replacement of a halogen atom on the feed by another halogen atom, e.g., the substitution of a fluorine atom for a bromine atom. Suitable feedstocks for these reactions can be obtained in several ways and one procedure involves the reaction of a perhalogenated ethylene with 2,2,2-trifluoroethanol. The perhalogenated ethylenes have the formula $CF_2=CX_2$ in which X is fluorine or chlorine. These reactions can be conducted in the presence of potassium hydroxide and a small amount of α-pinene. Suitable temperatures for the reactions are generally in the range of about 30° to 50° C.

The chlorination or bromination of the ethers resulting from the foregoing reaction can be conducted with the use of molecular chlorine or bromine. Chlorine can be reacted conveniently at temperatures of about 50° to 60° C. in the presence of light. In the reaction gaseous chlorine can be passed into the liquid ether feed, and the chlorine can be added to the reactor at the approximate rate it reacts. If desirable, the reactor can be cooled to control the reaction temperature. Bromination of the ethers can be effected by passing a mixture of gaseous bromine and an inert gas such as nitrogen along with ether feed in the vapor phase through a reaction zone maintained at elevated temperatures, e.g. about 400° to 550° C. In either of these reactions systems the products can be separated by fractional distillation or gas chromatography techniques.

The ethers of this invention can be made by a fluorination process involving the use of molecular fluorine. For example $CF_3CH_2OCF_2CHFCl$ can then be converted to a mixture containing $CF_3CHFOCF_2CHFCl$, $CF_3CH_2OCF_2CF_2Cl$ and $CF_3CHFOCF_2CF_2Cl$, all compounds of the present inventions, by reaction with gaseous fluorine to replace one of the hydrogen atoms on the 1-carbon atom which bears two hydrogen atoms and/or replace the hydrogen atom on the 2-carbon atom bearing a chlorine atom. The fluorination can be accomplished by mixing the feed compound with carbon tetrachloride or other fluorine and/or chlorine-containing alkane solvents which are preferably perhalogenated, and then contacting the mixture with gaseous fluorine at reduced temperatures, e.g. below about 0° C., preferably about −20° to 0° C. Lower alkyl ethers which are perhalogenated with one or both of chlorine or fluorine may also be suitable solvents. Hydrogen fluorine is evolved from the reaction mixture during this fluorination procedure and the HF can be collected by passage of the evolved gases through a water scrubber. After a substantial amount of the feed ether has reacted, the desired products can be separated from the reaction mixture by gas chromatography. This fluorination procedure can be used to prepare various compounds of the invention from the corresponding ethers.

The following examples will serve further to illustrate the present invention.

EXAMPLE I

Preparation of the Intermediate $CF_3CH_2OCF_2CHF_2$

Tetrafluoroethylene (400 g.) was added as a gas at 300–500 psi to a stirred 1 liter autoclave containing a solution of potassium hydroxide (50 g.) in $CF_3CH_2O$ (400 cc.) and also a small amount of α-pinene (10 g.). The autoclave was heated to 40° C. to initiate the reaction. The reaction then proceeded smoothly with a slight exotherm and was maintained at 35°–45° C. The crude product was washed with water and then fractionally distilled to obtain 350 g. of $CF_3CH_2OCF_2CHF_2$, b.p. 55.5° C. at 760 mm.

EXAMPLE II

Preparation of $CF_3CHClOCF_2CF_2H$ $CF_3CH_2OCF_2CF_2H$ (140 g.) was reacted with chlorine gas at a temperature of 50°–60° C. in a glass apparatus in the presence of incandescent light. When 0.7 mole of chlorine per mole of ether had reacted, the crude product weighed 157 g. and contained 60% of $CF_3CHClOCF_2CF_2H$ as shown by gas chromatography. This product was separated and purified by fractional distillation and preparative vapor phase chromatography. The product analyzed as follows:

Calculated for $C_4H_2ClF_7O$: C, 20.5; H, 0185, b.p. 66° C. Found: C, 20.8; H, 1.03.

| | |
|---|---|
| Specific gravity | 1.5 |
| Vapor pressure | 175 mm. Hg./25°C. |
| Odor | slight |
| Flammability | non-flammable. |

The structure $CF_3CHClOCF_2CF_2H$ was confirmed by the n.m.r. and infrared spectra.

EXAMPLE III

Preparation of $CF_3CHBrOCF_2CF_2H$ $CF_3CH_2OCF_2CF_2H$ (110 g.) was reacted with bromine (125 g.) by passing a mixture of the two diluted with a stream of nitrogen through a 12 inch × 1 inch glass tube heated to 475° C. The effluent product was condensed in a "Dry Ice" trap and purified by fractional distillation and preparative gas chromatography to give $CF_3CHBrOCF_2CF_2H$., b.p. 80° C., $n_D^{25}$ 1.3155. This product analyzed as follows:

Calculated for $C_4H_2F_7BrO$: C, 17.4; H, 0.74. Found: C, 17.52; H, 0.73.

| | |
|---|---|
| Specific gravity | 1.8 |
| Vapor pressure | 100 mm. Hg./25°C. |
| Odor | not unpleasant |
| Flammability | non-flammable |

EXAMPLE IV

Preparation of $CF_3CHFOCF_2CF_2H$ $CF_3CH_2OCF_2CF_2H$ (100 g.) was fluorinated at −20° C. in $CCl_4$ (350 cc.) in a glass reactor using fluorine diluted with argon ($F_2$ at 80 cc./min. argon at 160 cc./min.). After 7 hours, conversion of the feed ether to $CF_3CHFOCF_2CHF_2$ was 28 mole %. The product of $CF_3CHFOCF_2CHF_2$ was isolated by distillation and preparative gas chromatography, b.p. 41° C., and analyzed as follows:

Calculated for $C_4H_2F_8O$: C, 22.0; H, 0.92. Found: C, 22.1; H, 0.9.

| | |
|---|---|
| Specific gravity | 1.4 |
| Vapor pressure | 430 mm. Hg./25°C. |
| Odor | None |
| Flammability | non-flammable |

The assigned structure was confirmed by the n.m.r. spectrum.

EXAMPLE V

Preparation of $CF_3CHFOCF_2CHCl_2$ and $CF_3CHFOCF_2CFCl_2$ $CF_3CH_2OCF_2CHCl_2$ (232 g.) (proposed as in Example I but using $CF_2 = CCl_2$ instead of $CF_2 = CF_2$) was fluorinated in Freon 113 ($CCl_3CF_3$) (850 cc.) at −20° C. in a glass reactor using fluorine diluted with argon, ($F_2$ at 80 cc./min., argon at 160 cc./min.). After 7 hours, 42% of the starting ether was converted to a mixture of $CF_3CHFOCF_2CHCl_2$ and $CF_3CH_2OCF_2$-$CFCl_2$. $CF_3CHFOCF_2CHCl_2$, b.p. 89° C., $n_D^{20}$ 1.3261, was isolated by gas chromatography and analyzed as follows:

Calculated for $C_4H_2Cl_2F_6O$: C, 19.19; H, 0.8. Found: C, 19.2; H, 0.88.

| | |
|---|---|
| Specific gravity | 1.54 |
| Vapor pressure | 58 mm. Hg./25°C. |
| Odor | etheral |
| Flammability | Non-flammable. |

The resulting mixture of fluorinated ethers can be further fluorinated using the same conditions to give additional quantities of $CF_3CHFOCF_2CFCl_2$, b.p. 75° C., which can be separated by gas chromatography. This product analyzed as follows:

Calculated for $C_4HCl_2F_7O$: C, 17.85; H, 0.37. Found: C, 18.10; H, 0.40.

| | |
|---|---|
| Specific gravity | 1.67 |
| Vapor pressure | 120 mm. Hg./25°C. |
| Flammability | non-flammable. |

EXAMPLE VI 2,2,2-Trifluoroethyl 1′,1′,2′-trifluoro-2′-chloroethyl ether ($CF_3CH_2OCF_2CHFCl$) (216.5 g., 1.0 m.) (prepared as in Example I but using $CF_2 = CFCl$ instead of $CF_2 = CF_2$) in 900 ml. of carbon tetrachloride was fluorinated at −15° C. in a glass flask using 33% fluorine in argon ($F_2$ at 80 cc./min., argon at 160 cc./min.) at a rate of 0.2 mole fluorine per hour. After 7 hours, 36% of the starting ether had been converted to fluorinated products, and the reaction mixture analyzed as follows:

| | |
|---|---|
| 0.9% | $CF_3CHF-O-CF_2CF_2Cl$ |
| 2.35% | $CF_3CH_2-O-CF_2CF_2Cl$ |
| 2.59% | $CF_3CHF-O-CF_2CHFCl$ |
| 5.56% | $CF_3CH_2-O-CF_2CHFCL$ |
| 88.53% | $CCl_4$ |

The products $CF_3CHF-O-CF_2CHFCl$, $CF_3CH_2OCF_2CF_2Cl$, and $CF_3CHFOCF_2CF_2Cl$ were separated from unreacted starting ether and were recovered by fractional distillation. These ether products were further purified by preparative gas chromatography. The preparative gas chromatography products separated were as follows:

| | |
|---|---|
| $CF_3CHFOCF_2CHFCl$, b.p. 65.5° C. | |
| Calculated for $C_4H_2ClF_7O$: F, 56.6 % | |
| | Found: F, 55.6 % |
| Specific gravity | 1.52 |
| Vapor pressure | 175 mm. Hg./25° C. |
| Odor | ethereal |
| Flammability | non-flammable |
| $CF_3CH_2OCF_2CF_2Cl$, b.p. 57° C. | |
| Calculated for $C_4H_2ClF_7O$: F, 56.6 % | |
| | Found: F, 56.7 % |
| Specific gravity | 1.48 |
| Vapor pressure | 240 mm. Hg./25° C. |
| Odor | ethereal |
| Flammability | non-flammable |
| $CF_3CHFOCF_2CF_2Cl$, b.p. 42.5° C. | |
| Calculated for $C_4HClF_8O$: F, 60.1 % | |
| | Found: F, 60.1 % |
| Specific gravity | 1.52 |
| Vapor pressure | 410 mm. Hg./25° C. |
| Flammability | non-flammable. |

The identity of each of these ether products was confirmed by the nuclear magnetic resonance (n.m.r.) spectrum.

EXAMPLE VII

Preparation of $CF_3CHBrOCF_2CHFCl$ $CF_3CH_2OCF_2CHFCl$ (104 g.) and bromine (85 g.) were vaporized in a stream of nitrogen at 15–20 l/hr. The gaseous mixture was then passed through a 1 inch × 12 inch glass tube at 475° C. The crude product (137 g.) was condensed in a "Dry Ice" trap and purified by fractional distillation and preparative gas chromatography. The product $CF_3CHBrOCF_2CHFCl$ had b.p. 109° C., $n_D^{20}$ 1.3525 and analyzed as follows:

Calculated for $C_4H_2BrClF_6O$: C, 16.25; H, 0.68. Found: C, 16.34; H, 0.57.

| | |
|---|---|
| Specific gravity | 1.9 |
| Vapor pressure | 30 mm. Hg./25°C. |
| Odor | not unpleasant |
| Flammability | non-flammable |

The structure of the product ether was confirmed by the n.m.r. and infrared spectra.

In order to determine the potency of the ethers of the present invention as inhalation anesthetics in combination with oxygen, tests were carried out on mice. The compounds tested were at least 99.5 % pure as determined by vapor phase chromatography. In the tests, the ether compound is administered to test mice by a standard procedure in which a measured quantity of the agent is placed in a laboratory jar and allowed to completely vaporize so as to give a calculated vapor concentration. The test mice are then quickly placed in the jar and observed. Anesthesia is determined by observing the righting reflex of the mice. Recovery time is measured beginning when the mice are transferred from the test jar to room air and ending when the mice are observed to be able to walk.

In such tests the 1,2,2,2-tetrafluoroethyl 1',1',2'-trifluoro-2'-chloroethyl ether induced a light level of anesthesia in 53 seconds when used at a vapor concentration of 2%. The induction was accompanied by brief excitement. Recovery required 75 seconds. At 2.5% concentration the induction period lasted 40 seconds and recovery required 52 seconds. There was brief excitement during induction and recovery. Respiration slowed to 64 per minute during maintenance of the anesthesia, but the color of the mice remained good.

Thus it is seen that the compound 1,2,2,2-tetrafluoroethyl 1',1',2'-trifluoro-2'-chloroethyl ether exhibited good anesthetic properties in inhalation anesthetic-susceptible mammals, giving rapid induction and recovery and moderate respiratory depression. The compound is soda lime stable, and lends itself well to effective use as an inhalant anesthetic in respirable mixtures containing life-supporting concentrations of oxygen.

Using a 2.5% vapor concentration of 2-chloroperfluoroethyl 2',2',2'-trifluoroethyl ether a low level of anesthesia was induced with hyperexcitability in 7 minutes. One of five mice died of respiratory failure during maintenance of the anesthesia. The animals were excitable in recovery and one became cyanotic, but survived.

Using a 1.25% vapor concentration of 2-hydroperfluoroethyl 1'-chloro-2'-2'-2'-trifluoroethyl ether, very light anesthesia was induced in the mice in 4.7 minutes. Respiration was slowed and animals rose to their feet when stimulated. At 2.5% concentration there was deep anesthesia in 1.3 minutes; recovery required 1.9 minutes. Respirations were abdominal during maintenance of the anesthesia, and the animals were hyperflexic and twitching during recovery. At 5% concentration the induction required 0.5 minute and the recovery took 3.9 minutes. The anesthesia was very deep at this concentration, one mouse in five arching its back during maintenance, and two in five arching theirs during recovery. There was jumping and twitching, and respiration was very depressed. Recovery was accompanied by marked tremors.

The compound 1-bromo-1-hydroperfluoroethyl 2'-hydroperfluoroethyl ether when used at 1.0% vapor concentration induced anesthesia in 1 minute 14 seconds; recovery therefrom required 3 minutes 12 seconds. Maintenance at this concentration was marked by motor activity at the start, leading to flaccidity and much respiratory depression. At 1.5% vapor concentration anesthesia was induced in 1 minute 8 seconds and recovery required 4 minutes 2 seconds. Induction was accompanied by much excitement. Maintenance proceeded as with 1% concentration, with the respiration rate being depressed to 20 per minute. At 2.5% vapor concentration there was marked excitement on induction, which required 43 seconds, and the respiration rate fell to 16 per minute. Recovery took 6 minutes 37 seconds.

Using 1-bromo-2,2,2-trifluoroethyl 2'-chloro-1',1',-2'-trifluoroethyl ether at 0.25% vapor concentration required 2 minutes 32 seconds to induce a light anesthesia with moderate respiratory depression during maintenance. Recovery took 6 minutes 13 seconds. At 0.5% concentration the induction occurred in 2 minutes 35 seconds and the recovery in 4 minutes 58 seconds. The excitement phase during induction was long, and moderate respiratory depression was observed during maintenance. At 0.75% concentration the inducement required 1 minute 16 seconds; again it was with excitement. The respiration rate fell to 40–60 per minute during maintenance. Recovery took 9 minutes. A level of 2.5% vapor concentration was lethal to all of the test mice.

Using 0.5% vapor concentration of 2,2-dichloro-1,1-difluoroethyl 1',1',2',2'-tetrafluoroethyl ether, induction of a very light anesthesia required 1 minute 29 seconds and recovery therefrom took 52 seconds. The induction was accompanied by mild excitement. At a level of 1.0% a light anesthesia was induced, again with mild excitement, in 35 seconds. Respiration was jerky and gasping during maintenance. Recovery required 3 minutes 24 seconds. Smooth induction occurred in 10 seconds when using 2.5% vapor concentration. There was some respiratory depression during maintenance and mild cyanosis in recovery. The recovery took 9 minutes and the mice were sluggish afterwards.

At a vapor concentration of 5%, the compound 1,2,2,2-tetrafluoroethyl 1',1',2'-trifluoro-2',2'-dichloroethyl ether induced anesthesia in the test mice in 1 minute 30 seconds. The animals were restless in maintenance, with gasping, jumping, urination, and some cyanosis. The recovery was with excitement and required 35 seconds.

The compounds 2-chloro-1,1,2,2-tetrafluoroethyl 1',2',2',2'-tetrafluoroethyl ether and 1,2'-dihydroperfluorodiethyl ether were both tested at 2.5% and 5.0% vapor concentrations and were observed to have a sedative effect on the mice; but they did not induce anesthesia.

Examples of other halogenated diethyl ethers which I have considered as possible anesthetics are listed below, but none was satisfactory.

| Compound | Properties |
| --- | --- |
| $CF_3CH_2—O—CF_2CHFCl$ | Convulsant |
| $CF_3CH_2—O—CF_2CF_2H$ | Convulsant |
| $CF_3CHCl—O—CF_2CHFCl$ | Convulsant |
| $CF_3CH_2—O—CH_2CF_3$ | Convulsant |
| $CF_3CH_2—O—CF_2CH_2F$ | Convulsant |
| $CF_3CH_2—O—CF_2CHFBr$ | Anesthetic, convulsant properties. |

The effective amount of the compounds of this invention to be employed depends on the level of anesthesia to which the mammal is to be brought, the rate at which anesthesia is to be induced, and the length of time over which anesthesia is to be maintained. Minor volume percentages, for example about 0.25 to 5%, or somewhat more, of the compounds in respirable mixtures containing life-supporting amounts of oxygen can be employed. The amount used should be sufficient to provide a significant anesthetic effect, but not so much as to produce unacceptable deleterious side effects. The person controlling the anesthesia can easily regulate the amount of the ether to be used, starting with a small amount, e.g. about 0.25%, and gradually increasing the amount until the desired plane of anesthesia is reached. By then monitoring the physical properties of the mammal, as is the usual procedure, the duration and plane of anesthesia can be readily controlled.

It should be understood that the foregoing disclosure relates to preferred embodiments of the invention and that it is intended to cover all changes and modifications of the examples of the invention herein chosen for the purpose of the disclosure which does not constitute departure from the spirit and scope of the invention.

It is claimed:
1. The compound having the formula $CF_3CHFOCF_2CHFCl$.

* * * * *